(12) United States Patent
Wehde

(10) Patent No.: US 6,384,295 B2
(45) Date of Patent: *May 7, 2002

(54) DUCT TAPE BANDAGES

(76) Inventor: Wayne Wehde, 25625 Rt. 134, Ingleside, IL (US) 60041

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/412,093

(22) Filed: Oct. 4, 1999

(51) Int. Cl.[7] ................................................ A61F 13/00
(52) U.S. Cl. .............................. 602/54; 602/41; 602/56
(58) Field of Search ................................ 206/440, 441; 602/41–59; D24/189

(56) References Cited

U.S. PATENT DOCUMENTS

| | | | | |
|---|---|---|---|---|
| 2,823,672 A | * | 2/1958 | Schladermundt et al. | 602/57 |
| 3,007,571 A | * | 11/1961 | Marinaro | 206/441 |
| 3,256,881 A | * | 6/1966 | Stenvall | 206/441 |
| 4,545,843 A | * | 10/1985 | Bray | 156/322 |
| 4,655,209 A | * | 4/1987 | Scott | 602/41 X |
| 5,099,832 A | * | 3/1992 | Ward | 602/57 |

* cited by examiner

Primary Examiner—Kim M. Lewis
(74) Attorney, Agent, or Firm—Michael I. Knoll

(57) ABSTRACT

The present invention 10 discloses a bandage 10 having a strip of durable material, such as duct tape 24, having pressure sensitive adhesive 30 applied to its underside further having a sterilized gauze pad 20 attached thereto. The bandage has a shorter 12 and a longer side 14 and a removable release liner 26 thereon along with possibly a removable sterile cover having a tear strip thereon for easy removal thereof.

1 Claim, 7 Drawing Sheets

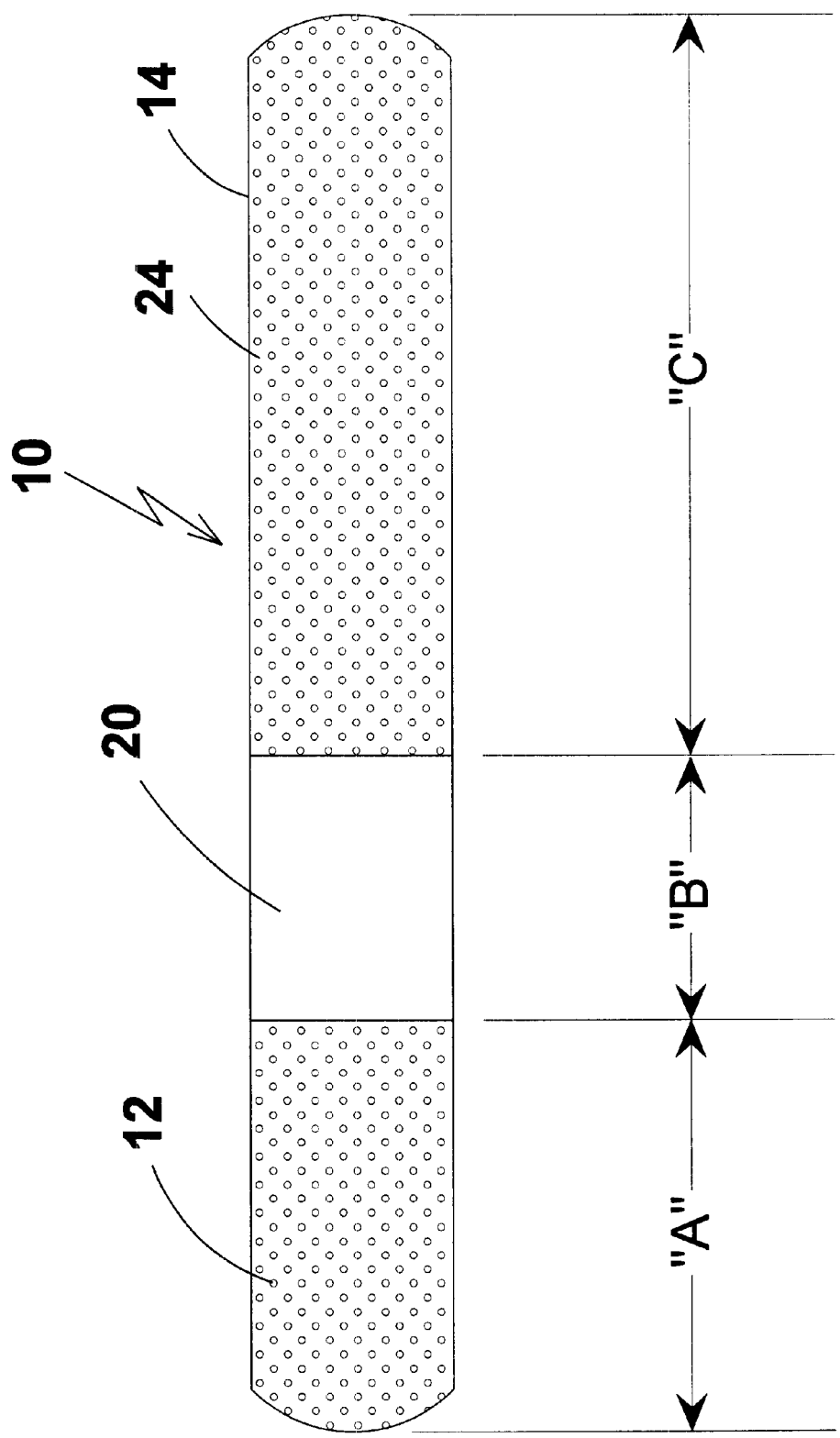

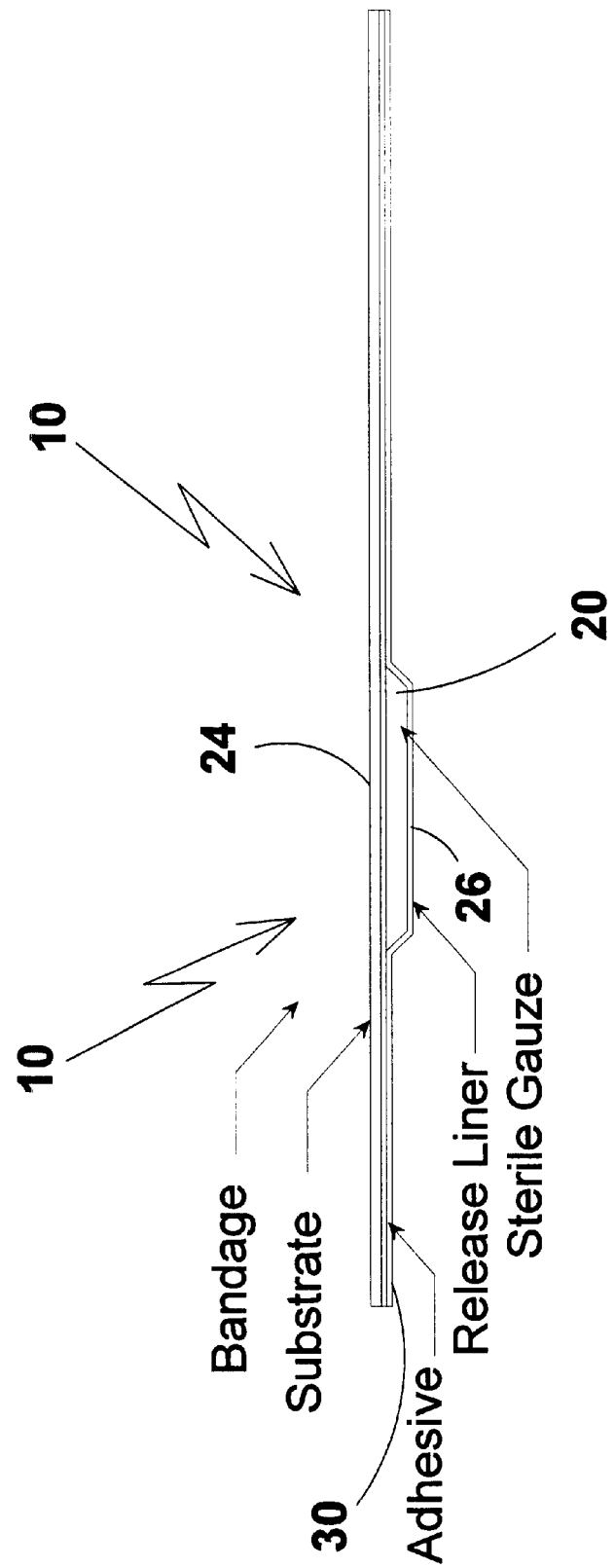

DUCT TAPE BANDAGES

BACKGROUND OF THE INVENTION

1. Field of the Invention

The present invention relates generally to bandages and, more specifically, to a bandage comprising a strip of durable material such as duct(tape having a suitable pressure sensitive adhesive applied to the underlying side whereupon a sterile gauze pad is affixed off-center thereto. In addition said bandage has removable release liners protecting the adhesive layer until desired use. The bandage can be encapsulated in a sterile removable covering such as paper having a tear strip for easy removal therefrom.

2. Description of the Prior Art

There are other bandages designed for wound dressing. Typical of these is U.S. Pat. No. 5,310,402 issued to Rollband on May 10, 1994.

Another patent was issued to Geng on Jun. 10, 1997 as U.S. Pat. No. 5,637,080. Yet another U.S. Pat. No. 5,891,074 was issued to Cesarczyk on Apr. 6, 1999 and still yet another was issued on Jan. 20, 1998 to Ward as U.S. Pat. No. 5,709,651.

A tape for attaching bandages, with non-adhesive tabs at each end for easy manipulation and removal while wearing gloves is disclosed. Also disclosed are tapes with target markings for location of a puncture wound, tapes with pressure disks or plates attached, and methods of making and using tapes.

An external wound dressing having a cover which is reversibly movable to an open position exposing the wound from a closed position covering the wound thereby enabling selective viewing of the wound without removing the wound dressing from the individual.

A pressure wound dressing has a flexible support layer a pressure exerting support member attached to and extending from one side of the flexible support layer and, preferably a layer of pliant absorbent material attached to tile pressure exerting support member. The flexible support layer has an adhesive layer on the side from which the support member extends. Perferably, a removable liner is positioned on the adhesive layer opposite to the support layer. The pressure exerting support member preferably is formed from a sheet of material to provide two surfaces to provide two surfaces oriented at an angle with respect to each other.

An adhesive dressing comprising a backing layer, a pressure sensitive adhesive thereon and a support layer attached to the non-adhesive surface of the backing layer characterized in having an additional edge strip component on the adhesive surface to aid adhesion of the dressing to the skin.

While these bandages for would dressing may be suitable for the purposes for which they were designed, they would not be as suitable for the purposes of the present invention, as hereinafter described.

SUMMARY OF THE PRESENT INVENTION

The present invention discloses a bandage having a strip of durable material, such as duct tape, having pressure sensitive adhesive applied to its underside further having a sterilized gauze pad attached thereto. The bandage has a shorter and a longer side and a removable release liner thereon along with possibly a removable sterile cover having a tear strip thereon for easy removal thereof.

A primary object of the present invention is to provide a wound dressing consisting of a durable substrate material having an off-center sterile dressing.

Another object of the present invention is to provide a bandage consisting of a durable substrate material such as duct tape.

Yet another object of the present invention is to provide a bandage consisting of a durable substrate material such as duct tape having an adhesive layer on one side.

Still yet another object of the present invention is to provide a bandage consisting of a durable substrate material such as duct tape having an adhesive layer on one side having an off-center sterile member attached thereto.

Another object of the present invention is one side is longer than the average bandage to obtain a double wrap around on small appendages and a complete wrap on larger appendages.

Yet another object of the present invention is to provide a bandage consisting of a durable substrate material such as duct tape having an adhesive layer on one side having an off-center sterile member attached thereto having releasable lining members covering the adhesive layer until desired use.

Still yet another object of the present invention is to provide a bandage encapsulated in a sterile package. Said bandage consisting of a durable substrate material such as duct tape having an adhesive layer on one side having an off-center sterile member attached thereto having releasable lining members covering the adhesive layer until desired use.

Additional objects of the present invention will appear as the description proceeds.

The present invention overcomes the shortcomings of the prior art by providing a bandage comprising a strip of durable material such as duct tape having a suitable pressure sensitive adhesive applied to the underlying side whereupon a sterile gauze pad is affixed off-center thereto. In addition said bandage has removable release liners protecting the adhesive layer until desired use. The bandage can be encapsulated in a sterile removable covering such as paper having a tear strip for easy removal therefrom.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which:

FIG. 6 is a diagrammatic illustration of the present invention, showing a perforated heavy duty substrate material having a shorter adhesive strip "A" then adhesive strip "C" because of the offset placement of the sterile gauze member "B".

FIG. 7 is a side view of the present invention. Shown is a bandage having a substrate strip made of a heavy durable material such as duct tape having a pressure sensitive adhesive applied to the underlying side having a sterile gauze pad affixed off-center thereto. Also shown is removable release liners protecting the adhesive layer until desired use. The bandage can be encapsulated in a sterile removable covering such as paper having a tear strip for easy removal therefrom.

LIST OF REFERENCE NUMERALS

Figure 1:
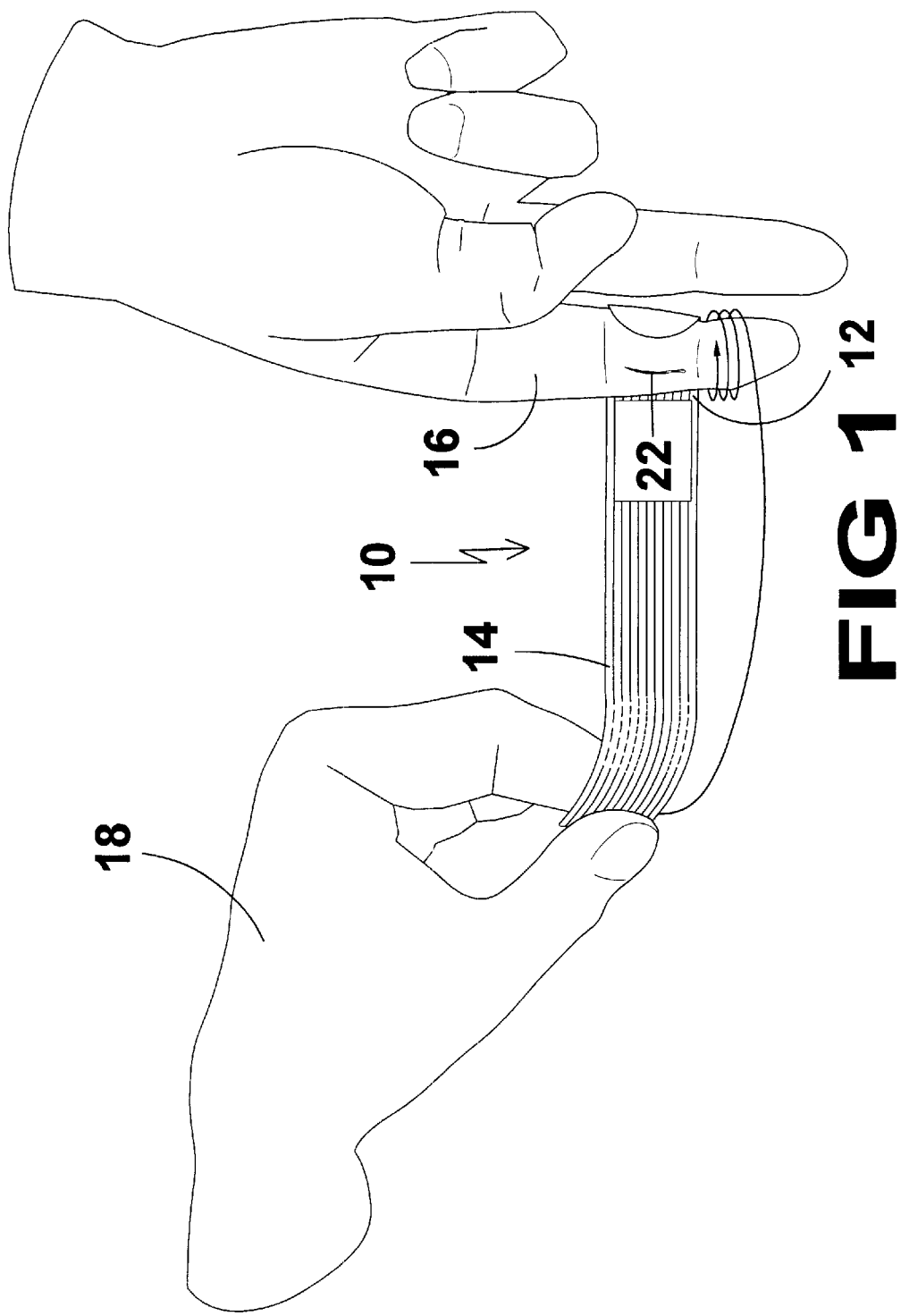
FIG. 1 is a perspective view of the present invention in use. Shown is a bandage with a short adhesive strip on one end and a longer strip on the other whereby said bandage can be used on fingers as well as larger areas.

With regard to reference numerals used, tile following numbering is used throughout the drawings:

10 present invention
12 short adhesive strip
14 long adhesive strip
16 finger
18 hand
20 gauze pad
22 cut
24 duct tape
26 releasable liner
28 forearm
30 adhesive
32 joinder line

DESCRIPTION OF THE PREFERRED EMBODIMENT(S)

In order that the invention may be more fully understood, it will now be described, by way of example, with reference to the accompanying drawings in which FIGS. 1 through 7 illustrate the present invention being a duct tape bandage.

Turning to FIG. 1, shown therein is a perspective view of the present invention 10 in use. Shown is a bandage 10 with a short adhesive strip 12 on one end and a longer strip 14 on the other whereby the bandage 10 can be used on fingers 16 as well as larger areas. The bandage 10 is shown being wrapped around finger 16 by hand 18 to cover cut 22.

Figure 2:
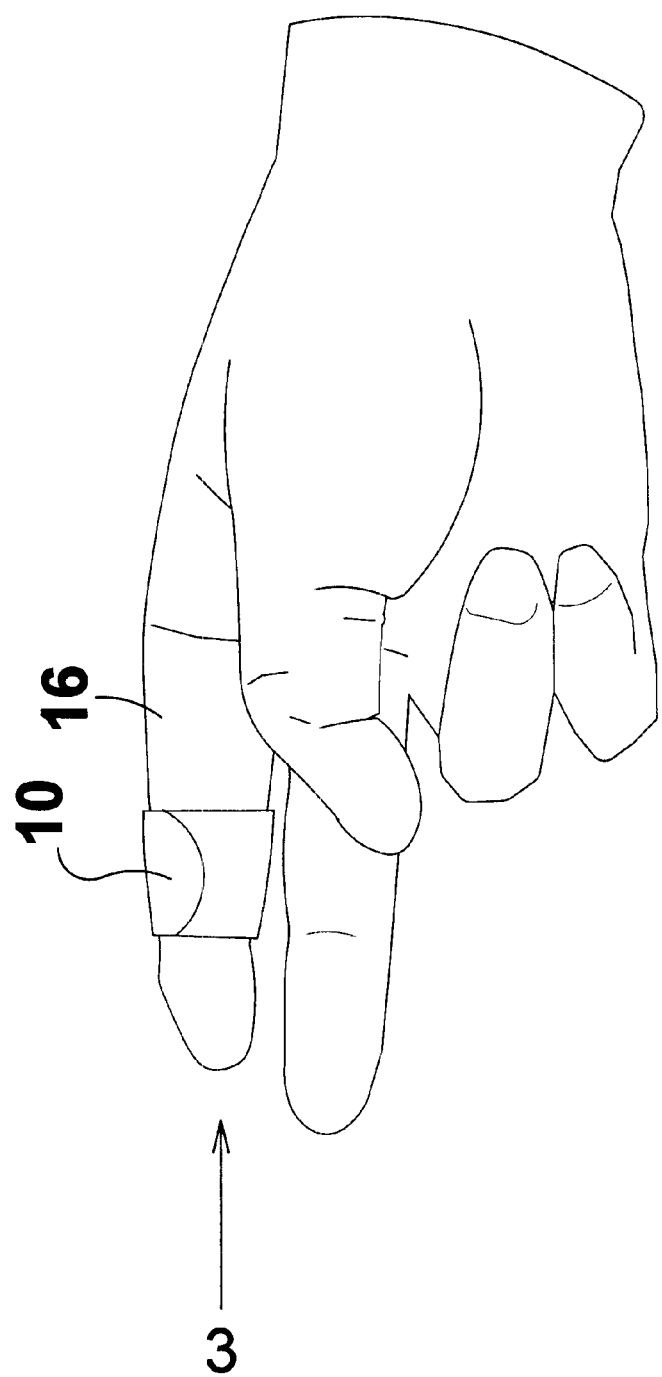
FIG. 2 is a perspective view of the present invention iii use. Shown is the completed application of the bandage as shown started in FIG. 1.

Turning to FIG. 2, shown therein is a perspective view of the present invention 10 in use. Shown is the completed application of the bandage 10 as shown started in FIG. 1 as it has been wrapped around finger 16.

Figure 3:
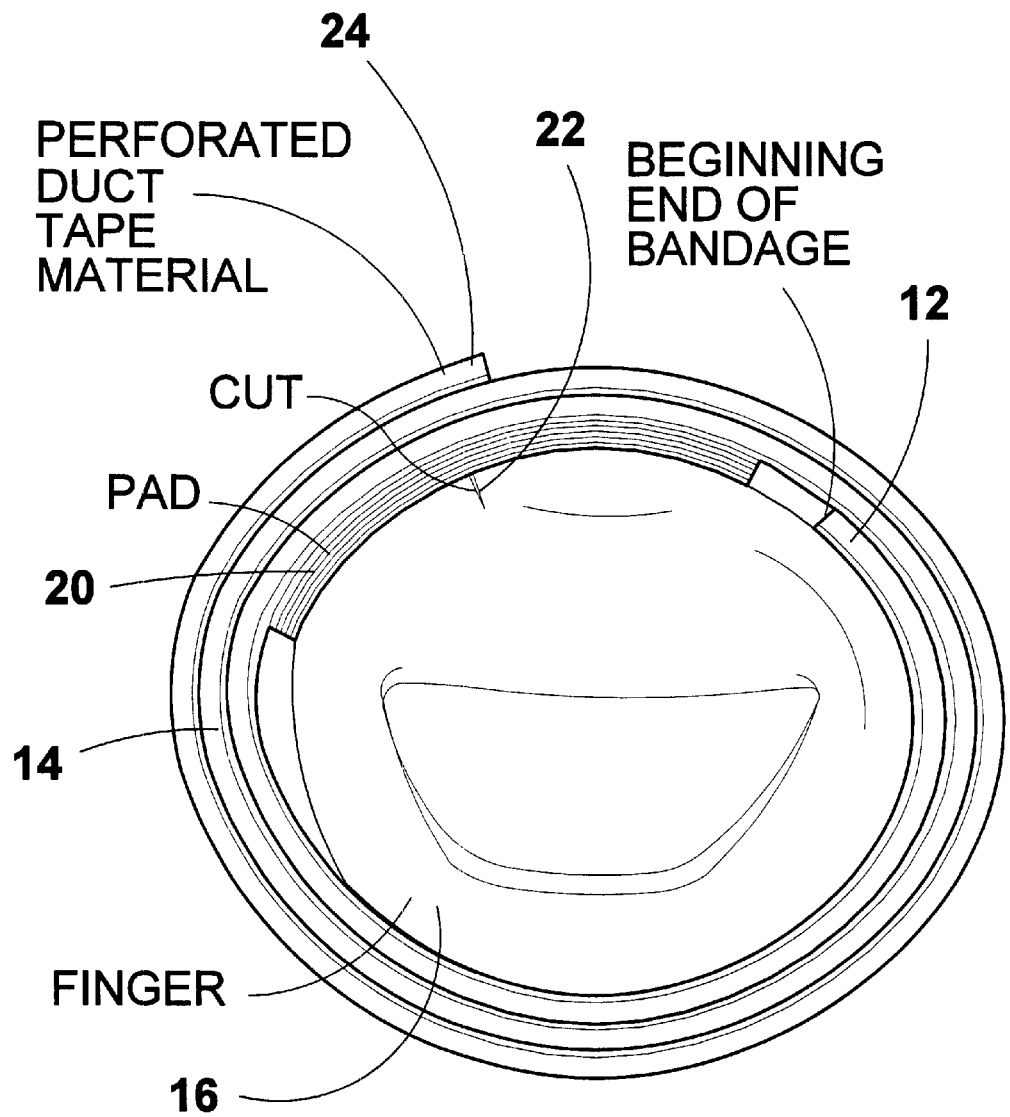
FIG. 3 is an enlarged end view of the applied bandage, taken from FIG. 1 as indicated. The bandage having an offset sterilized gauze pad has one short strip of adhesive for applying the bandage to smaller appendages such as finger and the larger adhesive strip can be wrapped around as needed.

Turning to FIG. 3, shown therein is an enlarged end view of the applied bandage 10, taken from FIG. 1 as indicated. The bandage 10 has an offset sterilized gauze pad 20 having one short strip 12 of adhesive for applying the bandage to a cut 22 on smaller appendages such as finger 16 and the larger adhesive strip 14 can be wrapped around as needed. The adhesive strips 12, 14 may be made of perforated duct tape material.

Figure 4:
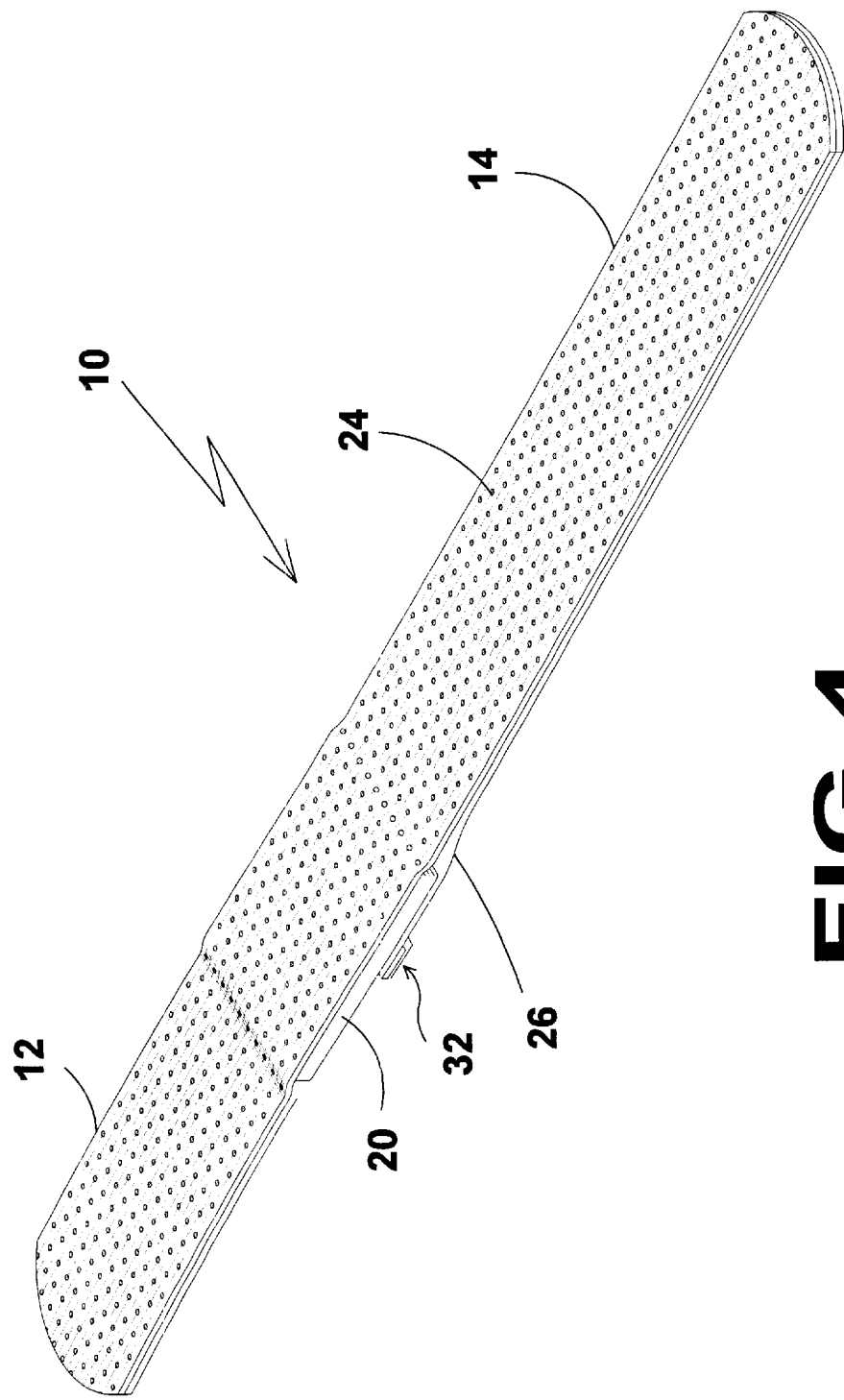
FIG. 4 is a perspective view of the present invention showing the perforated durable substrate material, such as duct tape having an off-center sterile gauze pad.

Turning to FIG. 4, shown therein is a perspective view of the present invention 10 showing the perforated durable substrate material 24, such as duct tape, having an off-center sterile gauze pad 20 along with the short side 12 and long side 14. A releasable liner 26 is also shown having a joinder line 32 between the two portions of the releasable liner 26 intermediate of pad 20.

Figure 5:
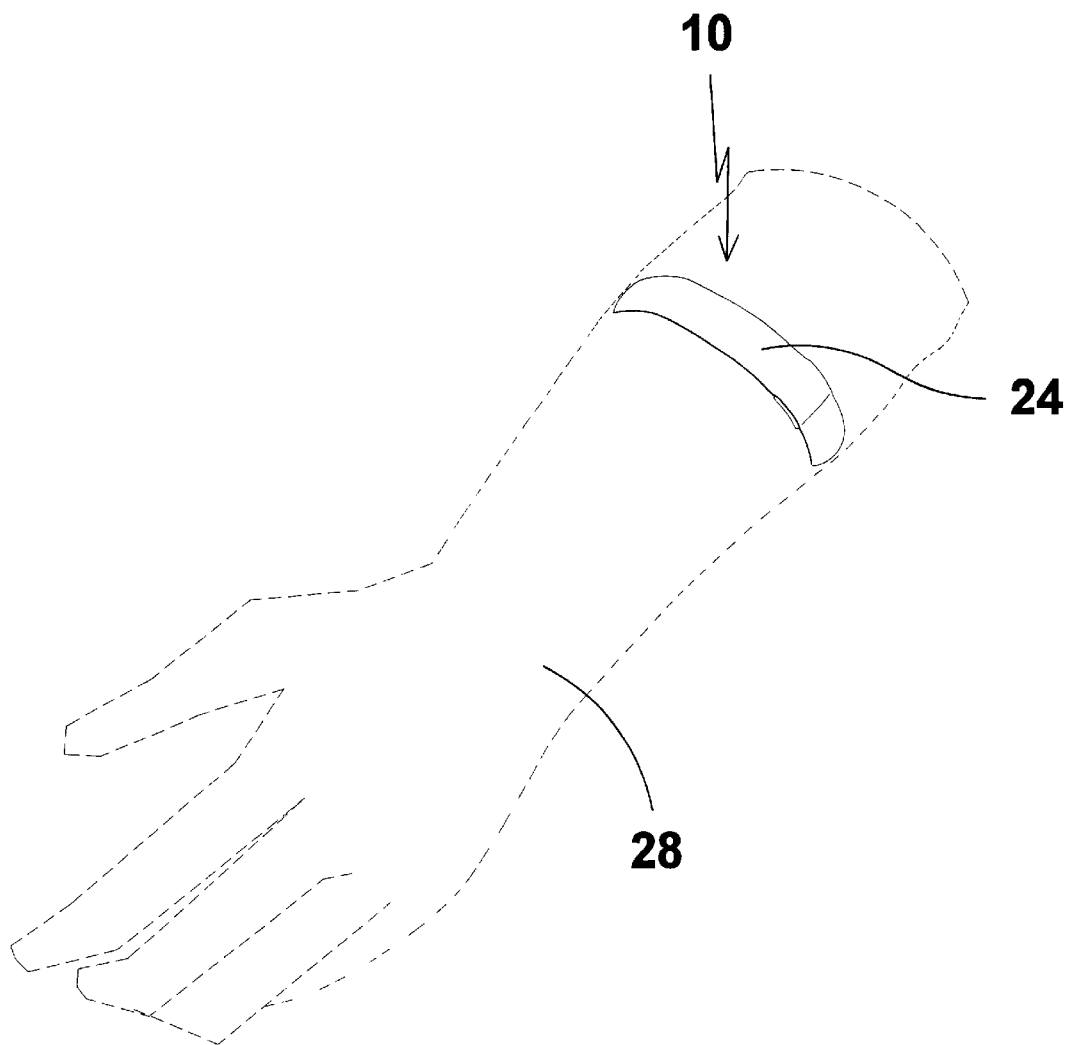
FIG. 5 is a perspective view of another application of the present invention. Where the area of the wound is on the forearm and the application of the bandage will provide a more durable sterilized covering due to the enlarged heavy duty substrate material.

Turning to FIG. 5, shown therein is a perspective view of another application of the present invention 10. Where the area of the wound is on the forearm 28, the application of the bandage 10 will provide a more durable sterilized covering due to the enlarged heavy duty duct tape substrate material 24.

Turning to FIG. 6, shown therein is a diagrammatic illustration of the present invention 10, showing a perforated heavy duty substrate material 24 having a shorter adhesive strip "A" 12 then longer adhesive strip "C" 14 because of the offset placement of the sterile gauze member "B" 20 which is about ⅓ the distance from end "A" to end "C".

Turning to FIG. 7, shown therein is a side view of the present invention 10. Shown is a bandage 10 having a substrate strip 24 made of a heavy durable material such as duct tape having a pressure sensitive adhesive 30 applied to the underlying side having a sterile gauze pad 20 affixed off-center thereto. Also shown is removable release liner 26 protecting the adhesive layer 30 until desired use. The bandage 10 can be encapsulated in a sterile removable covering such as paper having a tear strip for easy removal therefrom.

What is claimed to be new and desired to be protected by letters patent is set forth in the appended claims:

I claim:

1. An apparatus for a bandage strip, consisting of:
  a) a perforated backing material made of duct tape having first and second ends and of sufficient length to obtain a double wrap around a finger and a complete wrap around larger appendages;
  b) a pressure sensitive adhesive directly on the underside of said backing material disposed about ⅓ of the distance between said first and second ends from said first end;
  c) a gauze pad attached to said pressure sensitive adhesive;
  d) a releasable liner protecting said pressure sensitive adhesive and said gauze pad positioned on the side of said pressure sensitive adhesive opposite to said backing material; and,
  e) said releasable liner further comprising a first and second portion, and said first and second portions have a joinder line disposed intermediate of and along one side of said gauze pad.

* * * * *